Nov. 14, 1967 E. B. FITZGERALD Plant Pat. 2,777
CATTLEYA ORCHID PLANT
Filed June 20, 1966
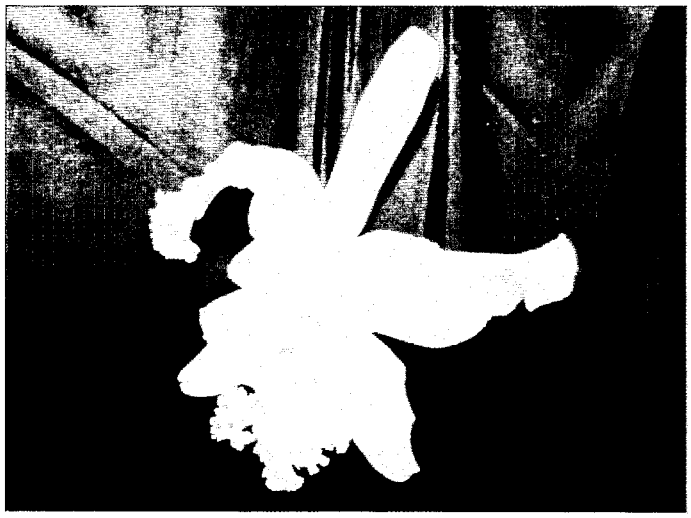
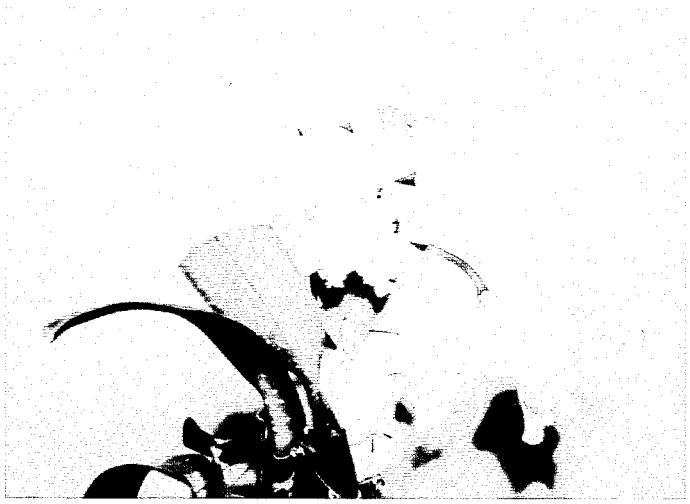
INVENTOR
ELIZABETH BACON FITZGERALD
BY Bayard H. Michael
ATTORNEY United States Patent Office Plant Pat. 2,777
Patented Nov. 14, 1967

2,777
CATTLEYA ORCHID PLANT

Elizabeth Bacon Fitzgerald, 3150 E. Kenwood Blvd., Milwaukee, Wis. 53211

Filed June 20, 1966, Ser. No. 559,688
1 Claim. (Cl. Plt.—68)

The present invention relates to a new and distinct variety of Cattleya orchid plant which was originated as a seedling selected from the, as yet, unnamed cross having as parents the Cattleya variety known as "Beverly Boswell" (Ryerson 507) with the Cattleya variety known as "Claris" (Patterson 419).

The plant possesses a unique combination of characteristics which are outstanding and which distinguish it from its parents as well as from all other varieties of which I am aware:

(1) Large pure white flower size of good form with the head erect and calyx curled back gracefully, and the petals firm and erect;

(2) The color of the bloom as a whole is pure white, while the modified petal is white but tinted with cadmium 15 light orange yellow on the inner throat, with the dorsal portion of the labellum tube faintly shaded with the same color;

(3) The plant is characterized by a sweet, pungent fragrance which is quite strong for an orchid, and long lasting quality both on the plant and as a cut flower.

Asexual reproduction of my new orchid variety, as performed by division in my greenhouse, 3150 E. Kenwood Blvd., Milwaukee, Wis., shows the foregoing characteristics and distinctions are fixed and come true and are transmissible through succeeding propagations.

The accompanying drawing shows a typical specimen plant of my new variety as well as an individual flower on a somewhat enlarged scale as compared with the view of the plant, all as depicted in color as nearly true as it is reasonably possible to make the same in a color illustration of this character.

The following is a detailed description of my new Cattleya orchid variety, as based on observations of specimens, with color terminology in accordance with Ridgway's Color Standards and Nomenclature, except where general color terms of ordinary dictionary significance are obvious:

Breeding: Hybrid.
*Male parent.*—"Beverly Boswell."
*Female parent.*—"Claris."

Propagation: Holds its distinguishing characteristics through succeeding propagation by division.

*Plant*

Form: 30 centimeters high, good, vigorous appearance.
Blooming habit: Cluster; many flowers on one stalk.
Blooming season: Winter-spring observed in my greenhouse.
Foliage (mature):
*Size.*—Medium.
*Quantity.*—Abundant.
*Shape.*—Normal orchid shape.
*Texture.*—Upper side leathery, under side smooth.
*Pseudobulb.*—Slim and elongated, very shiny and smooth.
*Color.*—New foliage is light cress-green and shiny on upper side, considerably lighter on under side.

*Flower*

Bud:
*Size.*—Medium.
*Form.*—Pointed and quite long. Hot, damp weather speeds growth and faster blooming. Cool, damp weather is more favorable by reason of reduction of floral pathology.
*Color and character of growth.*—When sepals first divide they are sea foam green (Plate XXXI, Tone F) as listed in Ridgway's color and become sea foam yellow (Plate XXXI) when splitting of the bud occurs. The pointed edges of the bud possess dark cress-green tips as listed in Ridgway's color with white pigmentation more pronounced on lateral surfaces, especially at the basal aspect. When the petals unfurl they become more white and less green. When the bloom is grown, the green pigmentation gives way to the white and the three sepals appear green only at apical area and in parallel veination. The sepals are smooth around the edges but curl back at the front edges. Takes two to three days to bloom. Calyx, generously large, long, and smooth but indented in given areas, crescent or funnel shaped. When rubbed, an odor of sweet banana perfume is present. The peduncle or stalk is six centimeters long, being slender but vigorous, having a smooth aspect and light cress-green as listed in Ridgway's color (Plate XXXI) shading. With one bloom the peduncle is rigid and slender, but bends with two or more blooms. Upon opening of the bud it appears vigorous. Heat and dampness (overwatering) causes plant pathogenic results in the bloom.

Bloom:
*Size.*—Large, 12 to 19 centimeters. Dorsal sepal—10 x 2.5 centimeters. Lateral sepals—9 x 3 centimeters; 10 x 3 centimeters. Petals (common)—9.5 x 6.5 centimeters; 9.5 x 7.5 centimeters. Petal (modified)—9 x 6 centimeters.
*Borne.*—Several to a stalk, varying between one, two, and even three or four blooms, but two is more common. As the number of blooms on the stalk increases, the size decreases. Each bud is borne at intervals of 0.4 to 0.7 centimeter.
*Form.*—Large and vigorous and expanding. The sepals and petals are separated, flower has good form, the flower head erect, calyx curled back gracefully, petals firm and erect. The form of the bloom when first opening is crescent shaped, and progresses to a half open rain umbrella shape. The permanent bloom retains its form until the beginning of desiccation. The outer petals begin to curl back, especially at the frontal edges. There is considerable ruffling and twisting of the petal tips and labellum. There are two common petals and one modified petal at the center appearing in lip form. The stamens are centered inside the modified petal and are half hidden. The upper shaft of the stamen can be seen without manipulating the modified petal. The anthers are partially enclosed, each with an anther filament.
*Persistence.*—Excellent endurance, hang on and dry. Under normal conditions for Cattleya (cool and damp—55° to 60° F. and 60% humidity) last between four and five weeks. As a cut flower in normal conditions, lasts a favorably long time.
*Color.*—The following color compared with and listed in Ridgway's Color Book No. R5356 R54. Petals and sepals—pure white. Modified petal (labellum)—pure white with cadmium light orange yellow throat with white branching.

*Reproductive organs*

The top of the stamen: Pure white, partially enclosing four large deep chrome anthers in burnt umber-colored petaloids.

Pollen: Sticky with syrup and chrome yellow cells.

Style: Thick, medium in length in comparison to the blooms as a whole. The style appears like a pillar widening at the midsection. The stigma color is white. Syrup-like exudation and ovaries located below the style. Ovaries enclosed in the calyx.

I claim:

A new and distinct variety of Cattleya orchid plant, substantially as shown and described, characterized particularly by a pure white bloom having a cadmium light orange yellow tint on the inner throat of the modified petal, long lasting quality as a plant and as a cut flower, and a sweet, pungent fragrance which is quite strong for an orchid.

No references cited.

ROBERT E. BAGWILL, *Primary Examiner.*